(12) United States Patent
Bakaltcheva et al.

(10) Patent No.: US 6,436,705 B1
(45) Date of Patent: Aug. 20, 2002

(54) SHAPE STABILIZED ERYTHROCYTES

(75) Inventors: Irina B. Bakaltcheva, Springfield, VA (US); Alan S. Rudolph, Potomas; Barry J. Spargo, Baltimore, both of MD (US); Samuel B. Leslie, Alexandria; Thomas R. Groel, Manassas, both of VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/046,297

(22) Filed: Jan. 16, 2002

Related U.S. Application Data

(62) Division of application No. 09/022,341, filed on Feb. 11, 1998, now Pat. No. 6,358,678.
(60) Provisional application No. 60/038,424, filed on Feb. 18, 1997.

(51) Int. Cl.$^7$ .................................................. C12N 5/08
(52) U.S. Cl. ...................................... 435/372; 435/366
(58) Field of Search ........................... 435/2, 374, 533, 435/325, 93.7 B, 366, 372

(56) References Cited

U.S. PATENT DOCUMENTS

| | | |
|---|---|---|
| 4,287,087 A | 9/1981 | Brinkhous et al. |
| 4,711,852 A | 12/1987 | Jacobson et al. |
| 4,874,690 A | 10/1989 | Goodrich, Jr. et al. |
| 5,171,661 A | 12/1992 | Goodrich, Jr. et al. |
| 5,178,884 A | 1/1993 | Goodrich, Jr. et al. |
| 5,309,723 A | 5/1994 | Thomas et al. |
| 5,340,592 A | 8/1994 | Goodrich, Jr. et al. |
| 5,364,932 A | 11/1994 | Hsia |
| 5,476,764 A | 12/1995 | Bitensky |
| 5,690,963 A | 11/1997 | Spargo et al. |
| 6,358,678 B1 | 3/2002 | Bakaltcheva et al. |

FOREIGN PATENT DOCUMENTS

| | | |
|---|---|---|
| EP | 0 181 033 | 5/1986 |

OTHER PUBLICATIONS

Crowe et al, Effects of Carbohydrates on Membrane Stability at Low Water Activities, Biochimica et Biophysica Acta. 769, (1984) 141–150.

Deuticke et al, Formation of Aqueous Pores in the Human Erythrocyte Membrane After Oxidative Cross–linking of Spectrin by Diamide, Biocheimica et Biophysica Acta 731 (1983) 195–210.

Thirion et al, Circular Dichroism Studies of Freeze–Drying–Induced Conformational Changes in Human Hemoglobin, Biopolymers, vol. 22, 2367–2381 (1983).

Ruoho et al, A Disulfide–Bridge Bifunctional Imidoester as a Reversible Cross–Linking Reagent, Biochemical and Biophysical Research Communication, vol. 63, No. 2, 1975, pp. 417–423.

*Primary Examiner*—Jon P. Weber
*Assistant Examiner*—Patricia A Patten
(74) *Attorney, Agent, or Firm*—John J. Karasek; Jane B. Barrow

(57) ABSTRACT

One aspect of the present invention is a method for storing tissues and cells (typically erythrocytes) having the step of (1) stabilizing the cells with a reversible stabilizing agent. This method typically will have the additional steps of (2) loading the cells with a cryoprotectant, and typically (3) storing the cells in liquid, frozen, or dry state. This method will also typically have the additional step of (4) prior to use, reversing the stabilization reaction. Preferably, the erythrocytes are pre-treated with CO to complex the hemoglobin with CO. It is anticipated that a practical method according to the invention will include reoxygenation of the eryathrocytes, and also washing out reagents prior to in vivo use. Another aspect of the present invention is an erythrocyte that has had its shape stabilized by the reversible crosslinking of proteins in the erythrocyte, such as the structural proteins of the cytoskeleton. Another aspect of the invention is a population of such reversibly cross-linked erythrocytes. Another aspect of the invention is the in vivo use of such erythrocytes, after the reversal of the crosslinking reaction. The use of more gentle, reversible cross-linking as described below is desirable to result in the recovery of erythrocyte deformability and extended post-transfusion survival.

5 Claims, 5 Drawing Sheets

SHAPE STABILIZED ERYTHROCYTES

CROSS REFERENCE TO RELATED APPLICATION

This application is a divisional application of application Ser. No. 09/022,341, filed Feb. 11, 1998 now U.S. Pat. No. 6,358,678 which was a nonprovisional of provisional application Ser. No. 60/038,424, filed on Feb. 18, 1997.

BACKGROUND OF THE INVENTION

1. Field of the Invention

The present invention is related to the physicochemical modification of cells and tissues, in particular erythrocytes, by reversible crosslinking agents, to increase storage stability in liquid, frozen, and dry form.

2. Description of the Related Art

There is a continuing need in the art for methods to improve the shelf-life of tissues and cells, including especially erythrocytes (red blood cells or RBCs). Typically, erythrocytes are stored under refrigeration as packed cells. As refrigerated packed cells, erythrocytes have a shelf life of six weeks. It is a goal of the art to extend this shelf life.

Other methods for storing erythrocytes under consideration include freezing and lyophilization (freeze-drying). However, these methods put a great deal of stress on erythrocytes, leading to excessive hemoglobin loss.

For a method of storing erythrocytes, whether by refrigeration, freezing, or lyophilization, for subsequent mammalian (especially human) transfusion to be satisfactory, it is desired to satisfy certain criteria. These criteria include the following: (a) avoiding erythrocyte cell membrane rupture, and consequent hemoglobin loss; (b) maintaining the ability of erythrocytes to take up and release oxygen, which will include avoiding the oxidation of hemoglobin to methemoglobin (which does not take up oxygen); (c) avoiding the loss of cell deformability, so that erythrocytes may circulate through capillaries; and (d) maintaining the viability of these erythrocytes.

The field of cryobiology describes two fundamental strategies for freezing and freeze-drying of mammalian cells: the use of cryoprotectant solutes and cryofixatives. The earliest attempt to apply these strategies to the lyophilization of erythrocytes was explored by Maryman in the early 1960's. In this work human and rat erythrocytes were lyophilized using the polymer PVP as a cryoprotectant. These experiments resulted in little success and the effort was abandoned as no cellular recovery and hemoglobin droplet formation was reported. Almost 25 years later, a group of investigators led by Crowe and colleagues used cryoprotectant carbohydrates to stabilize membranes in the dry state toward the stabilization of erythrocytes. This method employed cryoprotectant carbohydrates as water-replacement molecules with polymers such as PVP to result in red cell stabilization to freeze-drying. Thus, the development of lyophilization media is based on mixtures of stabilizing carbohydrates and matrix stabilizing polymers. Early application of such mixtures to lyophilization of red cells by Goodrich et al. showed only limited success (Goodrich Jr et al., U.S. Pat. No. 4,874,690; Goodrich Jr and Williams C. M., U.S. Pat. No. 5,171,661; Goodrich Jr et al., U.S. Pat. No. 5,178,884). Erythrocytes lyophilized in concentrated glucose and 40% PVP showed osmotic fragility and upon reconstitution and washing the cells swelled to spherocytes and lysed.

A second strategy for the stabilization of biological structures for freeze-drying is the use of fixatives. Bode A and Read M (1995) have shown that platelets lightly treated with paraforn-aldehyde retain structural integrity and some hemostatic functionality after lyophilization and rehydration. The stabilization of platelets by this irreversible crosslinking agent also results in viral inactivation. Issues that remain to be addressed in the clinical development of these preparations is the preclinical efficacy in animal models of homeostasis, and the potential for toxicities associated with trace paraformaldehyde, which can increase membrane rigidity and change the rheological properties of the cells. The loss of red cell deformability by fixation could cause significant problems in the circulatory system due to their size and shear forces encountered upon transit through the microcirculation.

U.S. Pat. No. 4,711,852 teaches a method for preparing a blood gas-hemoglobin analysis control by stabilizing red blood cells with the crosslinking agent dimethyladipimidate (DMA). Higher degree of stability was achieved with the imidoester DMA as compared to other protein cross-linking agents (formaldehyde, sodium tetrathionate, diamide, diethyl oxydiformate and dimethyl suberimidate). However, these red blood cells could not be used for transfusion.

It is desirable to add cryoprotectants to erythrocytes prior to freezing, to protect them during freezing. Unfortunately, erythrocyte membranes have little or no permeability to many cryoprotectants, including sugars, including monosaccharides (e.g., glucose) and disaccharides (e.g., sucrose). Moreover, if erythrocyte membranes were made more permeable to such cryoprotectants, such permeability would likely be deleterious to erythrocyte viability in vivo.

In short, a method for treating erythrocytes for long term (>6 weeks) storage and subsequent transfusion should satisfy the following criteria: (a) the method should maintain the ability of the erythrocytes, at the time of transfusion, to take up and release oxygen, as part of the normal respiration process; (b) the method should maintain the ability of the erythrocytes, at the time of transfusion, to pass through the circulatory system, including the capillaries, by maintaining the ability of the erythrocytes to deform; (c) the method should not rupture the cell membrane of the erythrocytes; (d) the method should preserve, at the time of transfusion. the ability of the erythrocytes to metabolize sufficiently to maintain viability for some time after transfusion.

SUMMARY OF THE INVENTION

Accordingly, it is an object of this invention to improve the storage of tissues and cells.

It is a further object of this invention to improve the storage of erythrocytes.

It is a further object of this invention to improve the liquid storage of erythrocytes under refrigeration.

It is a further object of this invention to improve the storage of erythrocytes by freezing.

It is a further object of this invention to improve the storage of erythrocytes by lyophilization.

It is a further object of this invention to improve the ability to load cryoprotectants into erythrocytes.

It is a further object of this invention to protect the ability of erythrocytes to take up and release oxygen during long term storage.

It is a further object of this invention to protect the integrity of cell membranes during long term storage.

It is a further object of this invention to protect the metabolic viability of cells after long term storage.

It is a further object of this invention to protect the physical properties of cells (e.g., deformability) after long term storage.

It is a further object of this invention to achieve all of the foregoing objects in a manner that is consistent with viability and in vivo use of cells and tissues, including erythrocytes (e.g., for human and other mammalian transfusion).

These and additional objects of the invention are accomplished by the structures and processes hereinafter described.

One aspect of the present invention is a method for storing tissues and cells (typically eiythrocytes) having the step of (1) stabilizing the cells with a reversible stabilizing agent. This method typically will have the additional steps of (2) loading the cells with a cryoprotectant, and typically (3) storing the cells in liquid, frozen, or dry state. This method will also typically have the additional step of (4) prior to use, reversing the stabilization reaction. Preferably, the erythrocytes are pre-treated with CO to complex the hemoglobin with CO.

It is anticipated that a practical method according to the invention will include reoxygenation of the erythrocytes, and also washing out reagents prior to in vivo use.

Another aspect of the present invention is an erythrocyte that has had its shape stabilized by the reversible crosslinking of proteins in the erythrocyte, such as the structural proteins of the cytoskeleton.

Another aspect of the invention is a population of such reversibly cross-linked erythrocytes.

Another aspect of the invention is the in vivo use of such erythrocytes, after the reversal of the crosslinking reaction.

The use of more gentle, reversible cross-linking as described below is desirable to result in the recovery of erythrocyte deformability and extended post-transfusion survival.

BRIEF DESCRIPTION OF THE DRAWINGS

A more complete appreciation of the invention will be obtained readily by reference to the following Description of the Preferred Embodiments and the accompanying drawings in which like numerals in different figures represent the same structures or elements, wherein.

DETAILED DESCRIPTION OF THE PREFERRED EMBODIMENTS

Figure 1:
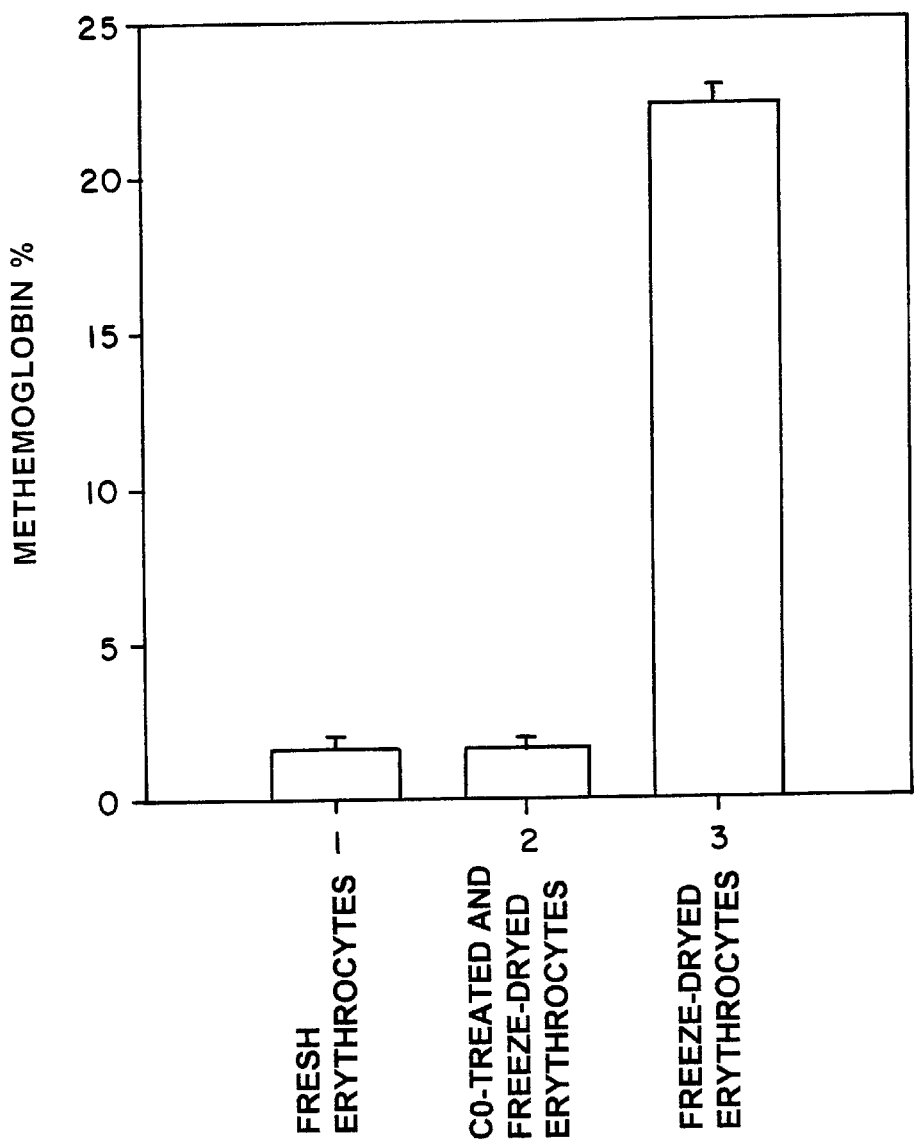
FIG. 1 shows methemoglobin formation during freeze-drying in various samples, under varying conditions.

The following are incorporated by reference herein, in their entireties, and for all purposes:

(a) Bakaltcheva et al., "Advantages of Diamide Treatment in Cryopreservation", Cryo-biology: International Journal of Low Temperature Biology 33 (1996) 675 (abstract);

(b) Bakaltcheva et al., "Shape-stabilizing agents protect red blood cells against freeze-thaw damage", Abstract Tu-Pos 403 from 40the Annual Meeting of th Biophysical Society, Feb. 17–21 1996;

(c) Bakaltcheva, I., Rudolph, A., and Spargo, B., "Shape Stabilizing Agents Protect Erythrocytes Against Freeze-Thaw Damage" (submitted to Cryo-Letters);

(d) Rudolph, et al., "Method for the preservation of red blood cells by lyophilization using glycerol or inositol with disaccharides", U.S. Pat. No. 5,242,792.

As noted above, the method for storing erythrocytes of the invention has the steps of (1) stabilizing the erythrocytes with a reversible stabilizing agent, (2) storing the erythrocytes for a storage time by refrigeration, freezing, or lyophilization, and (3) prior to use, reversing the stabilization reaction.

Cell Stabilization

As used herein, a reversible stabilizing agent is an agent that causes associations (typically covalent bonds) between structural proteins in erythrocytes (or other cells), where this association enhances the stability of the erythrocytes during storage by refrigeration. freezing, or lyophilization, and where this association can be broken by a chemical or physical process after storage in a manner that is consistent with the in vivo use of the erythrocytes (continued viability of the erythrocytes).

As used herein, "storage time" refers to a time between donation and in vivo use of erythrocytes. This time will be different for different storage methods, as will the conditions of storage. Liquid refrigeration of erythrocytes takes place under blood bank standards, and provides a shelf life of several weeks. Potentially, freezing and lyophilization could provide much longer storage times (months to years).

It has been discovered that for the purposes of the present invention, reversible crosslinking is advantageous compared to irreversible crosslinking. Cells can be stabilized by crosslinking and then subsequently (after a storage time) have their membrane properties restored. In particular, the cells can have their deformability restored. Decreased membrane deformability accompanies crosslinking. This effect has been found to be reversible when reversible crosslinking is performed. This is return of normal cell deformability for use in vivo is important for the microcirculation of erythrocytes through the capillaries. Additionally, erythrocyte deformability is important to erythrocyte survival in vivo.

An additional benefit to the use of reversible cross-linking agents in the present invention is that the toxic effects associated with the highly toxic compounds formaldehyde and paraform-aldehyde used in irreversible crosslinking can be avoided by applying gentle reversible crosslinking agents.

The reversible crosslinking agents used in the invention should satisfy several criteria: they should be biocompatible, they should react with the erythrocytes under biocompatible conditions, their crosslinking should be reversible, to return the erythrocytes to their previous deformable state consistent with in vivo use, the de-crosslinking reaction should take place under biocompatible conditions, they should reversibly increase the porosity of the erythrocytes to cryoprotectants, and the conditions that induce these changes in porosity should likewise be biocompatible. These crosslinking agents include SH-oxidizing agents such as diamide. and imidoesters that are amenable to reversibly crosslinking proteins in the membranes of erythrocytes. Imidoesters having a disulfide (-S-S-) group are reversible crosslinking agents.

It has been discovered that when a cell, such as an erythrocyte, is treated with one or more of the reversible crosslinking agents of the invention, these crosslinking agents will form linkages between structural proteins on the cell membrane. It has further been discovered that these linkages will stiffen the cell, stabilizing the shape of the cell. It has further been discovered that these shape-stiffened cells will develop pores suitable for the loading of cryoprotectant molecules such as sucrose into the cells. It has further been discovered that these shape-stabilized cells are able to withstand storage under harsher conditions than they could otherwise withstand, including refrigeration storage for extended periods of time, freezing, and lyophilization. It has further been discovered that after removal from storage (thawing in the case of frozen cells, and re-hydrating in the case of lyophilized cells), the cross linkages may be severed, and the properties of the cell are restored. It has further been discovered that the restored properties include deformability, which is essential to the ability of erythrocytes to navigate the bloodstream. It has further been discovered that erythrocytes lyophilized (typically down to about 10% residual $H_2O$) exhibit essentially complete (100%) recovery after rehydration. It has further been discovered that these cells return to essentially normal morphology, permeability, and (in the case of erythrocytes) oxygen transport ability.

The degree of crosslinking in a cell may be characterized not only by the absolute or relative number of cross linkages on the cell membrane, but also in terms of the changes in the properties of the cell membrane. For instance, resistance to lysis may be used as a benchmark to show the degree of crosslinking of cytoskeletal proteins in a cell membrane. The percentage of eiythrocytes in a sample that have lysed is given by the Equation:

$$\% \text{ Hemolysis} = [Abs_{sample}/Abs_{100\% hemolysis}] \times 100 \tag{1}$$

where $Abs_{sample}$=absorbance at 540 nm of the test sample and $Abs_{100\% hemolysis}$=absorbance at 540 nm of a completely lysed control sample (typically a control sample lysed in distilled water for several hours). It has been discovered that there is a preferred degree of crosslinking for the preservation of erythrocytes. It has been found that if % Hemolysis is too high (e.g., $\geq$ about 67%), the cells become unstable after reversal of the cross-linking. See FIG. 4, discussed below.

SH-oxidizing Agents:

Treatment with the SH-oxidizing agent diamide increases the stability of erythrocytes in liquid, frozen, or freeze-dried form, which appears to increase cytoskeleton stabilization. This crosslinking is accompanied by an increase in membrane permeability. Erythrocytes treated with SH-oxidizing agents can thus be loaded with what would otherwise be non-permeating disaccharides or slow permeating monosaccharides, which results in additional cryostabilization. Treatment with SH-oxidizing agents also increases erythrocnte shape stability when exposed to detergents such as Triton X-100. This additional stability against lysis by detergents will permit these cross linked erythrocytes to be treated with detergents to bacterial and viral inactivation. Cryostability and detergent red cell stability by treatment with SH-oxidizing agents was accompanied with decreased membrane deformability as measured by a 'gravity-driven' filtration assay. We have also explored the reversibility of the cross-linking reaction and demonstrated that normal deformability is restored after reversing the cross-linking reaction using reducing agents (see below). Accordingly, reversible cross-linking will be useful for the preservation of red cell structure and function and enhanced detergent stability for bacterial and viral inactivation. Detergents are commonly used to treat blood plasma. This invention now permits the use of such detergents on erythrocytes.

Bifunctional SH-oxidizing agents suitable for use as crosslinking agents in the present invention include diamide, tetrathionate, N,N'-phenylenedimaleimide, and 4,4-dithiopyridine. Skilled practitioners will recognize others.

Imidoesters:

Cleavable imidoesters have been recently developed which are designed to act under mild conditions resulting in minimal detectable changes-in protein and membrane structure. For example, treatment with penetrating Bifunctional imidoesters, does not affect the red cell glycolytic pathway or hemoglobin cooperatively, and stabilizes red cell membranes to sicklina and hypotonic lysis (Niehaus and Wold, 1970). Reversal of the imidoester cross-linking reaction was demonstrated as hypotonic lysis in water was restored following treatment with a reducing agent (Ruoho A et al., 1975). It has been discovered that treatment with the cleavable imidoester DTBP stabilizes erythrocytes against freeze-drying. The reversibility of the crosslinking reaction shows the usefulness of the cleavable imidoesters in developing preservation protocols.

Imidoesters suitable for use as crosslinking agents in the present invention include dimethyl-3,3-dithiobispropionimidate. 2HCL (DTBP), dimethyl-4,4 dithiobisbutyrimidate. 2HCL (DTBB), and dimethyl-5,5-dithiobisvalerimidate. 2HCL.

Other Reversible Crosslinking Agents:

Other reversible crosslinking reagents that may be of potential use in this invention include:

APDP(N-[4-(p-Azidosalicylarnido)butyl]-3-[2-pyridyl dithio]propionamide),

BASED(Bis-[b-(4-Azidosalicylamido)ethyl]disulfide),

BSOCOES (Bis[2-(succinimidooxicarbonyloxy)ethyl] sulfone).

Sulfo-BSOCOES(Bis[2-(sulfosuccinimidooxicarbonyloxy)ethyl]sulfone),

DPDPB (1,4-Di-[3-(2-pyrydyldithio)-propionamido)] butane),

DSP (Dithiobis[succinimidylpropionate]) or (Lomant's reagent),

DST (Disuccinimidyl tartarate),

DTSSP (3,3-Dithiobis[sulfosuccinimidylpropionate]),

EGS (Ethylene glycolbis-[succinimidylsuccinate]),

MBS (m-Maleimidobenzoyl-N-hydroxysuccinimide ester),

PDPH (3-[2-Pyridyldithio]propionylhydrazede),

SADP (N-succinimidyl[4-azidophenyl]1,3-dithiopropionate),

SAND (Sulfosuccinimidyl 2-[m-azido-o-nitrobenzamido]-ethyl-1,3-dithiopropionate), SASD Sulphosucciminidyl-2-[p-azidosalicylamido] ethyl-1,3-dithiopropionate), and SPDP (N-Succinimidyl-3-[2-pyridyldithyo]propionate).

Cryopreservative Carbohydrate Treatment

An additional benefit to the use of the reversible crosslinking agents of the present invention is that they tend to increase the porosity of cell membranes to carbohydrates that can protect the cells from damage during freezing. These cryopreservative carbohydrates include monosaccharides (such as glucose and fructose) and disaccharides (such as sucrose and treahalose). Other preferred carbo-hydrates include raffinose.

Carbohydrate loading is preferably done as follows: after crosslinking, cells are placed in a concentrated (between about 500 mM and 800 mM) aqueous solution of one or more carbohydrates, for at least about 12 to 24 hours, so that the cells can take up enough of the carbohydrates to provide protection to the cells during freezing.

CO Pretreatment:

Freeze-drying of hemoglobin leads to the formation of significant amount of methemoglobin. Circular dichroism studies for samples of hemoglobin freeze-dried with or without protectant have shown that the absence of a protector weakly influences the confirmation in the vicinity of the heme and increases the helicity of protein chains (Thirion C et al., 1983). Freeze-drying hemoglobin without denaturing and oxidizing it was made possible by the use of carbohydrates (Labrude PB et al., 1980). However, the preservative capacity of carbohydrates had been demonstrated on isolated, non-cellular hemoglobin. Since red cell membrane is non-permeable to disaccharides and only lowly permeable to monosaccharides, this limits the use of carbohydrates as protectants for intracellular hemoglobin. We explored CO-treatment as a means to prevent methemoglobin formation during freeze-drying. CO-treatment stabilizes hemoglobin in the CO-hemoglobin form by liganding CO. This prevents hemoglobin oxidation to methemoglobin during freeze-drying as shown in FIG. 1. Column 1 shows the methemoglobin content of fresh erythrocytes, column 2 shows the methemoglobin content of CO-treated and freeze-dried erythrocytes, and column 3 shows the methemoglobin content of freeze-dried erythrocytes. To reverse the CO-treatment, a hollow fiber oxygenator can be used.

It is preferred to perform the CO treatment under gentle conditions. We used an ice bath to keep the erythrocytes cool during CO pretreatment. It is preferred to use an antifoaming reagent during CO pretreatment, to reduce hemolysis. We used dimethyl polysiloxane as an antifoaming reagent during CO pretreatment.

Storage

Cells may be stored either under refrigeration or frozen.

Preferably, at least some degree of drying is performed prior to storage, because in principle removing moisture from the erythrocytes will help preserve them, allowing for storage for longer periods and/or storage at higher temperatures. However, it appears that if too much moisture is removed, the properties of the cells will be permanently degraded. Accordingly, it is preferred to not dry cells to less than about 10% moisture content.

Preparation for In Vivo Use After Storage

Before the treated cells are used in vivo, the cells should have their properties restored to a state consistent with in vivo use. At a minimum, this will entail reversing the crosslinking reaction to restore the cell membranes to as close to their original state as possible. The preferred reversible crosslinking agents will form disulfide (-S-S-) linkages between proteins, thereby stabilizing the shape of the cell. To reverse this stabilization, it is preferred to cleave these disulfide linkages with a mild reducing agent. Such a reducing agent should be biocompatible. Preferred reducing agents according to the invention include dithioerythritol (DTT), and other mild thiol-containing reducing agents. Such mild agents should avoid excessive (e.g., about 5%) cell lysis during reduction.

If CO pretreatment of erythrocytes has been used to prevent the formation of methemoglobin, this CO should be removed from the erythrocytes prior to transfusion, so that the cells can return to their normal oxygen transport functionality. Any conventional method for removing CO from erythrocytes for subsequent transfusion may be used.

Having described the invention, the following examples are given to illustrate specific applications of the invention, including the best mode now known to perform the invention. These specific examples are not intended to limit the scope of the invention described in this application.

EXAMPLE 1

TREATMENT OF ERYTHROCYTES WITH DIAMIDE

Materials and Methods

Reagents

All reagents were obtained from Sigma Chemical (St. Louis, Mo.), and were reagent grade or better.

Treatment of Cells

Packed human erythrocytes from healthy donors were obtained from the National Naval Medical Center (Bethesda, Md.) within 48 h of donation and used within 7 days. Packed erythrocytes were washed twice in phosphate buffer solution (PBS) then re-suspended in PBS (1 vol PBS:1 vol packed cells).

Washed cells were suspended in a medium containing: 80 mM KCI, 40 mM NaC, 10 mM Nap2HPO4/NaH2PO4, 40 mM sucrose and 6 mM diamide at pH8 (1 volume RBCs/9 volumes medium ). Samples were incubated for 60 min at room temperature. After the incubation was completed the unreacted diamide was removed by a washing procedure (it should be noted that the concentration of diamide applied may vary in the range of 1–10 mM diamide; the incubation time may vary between 30–90 min; the temperature may be elevated to 37° C.; electrolyte concentration, buffer concentration, and pH may also be varied within the limits of erythrocyte viability).

Freezing and Thawing:

Erythrocytes pre-treated with diamide were frozen immediately or after 3 h of incubation in the freezing medium (glucose 200 mM, raffinose 139 mM, sodium citrate 33 mM, sodium phosphate dibasic 12 mM, sodium phosphate monobasic 2.9 mM, ammonium phosphate 40 mM, adenine 2 mM) to allow loading with glucose. Freezing was carried out at −20° C. in a freezer for 30 min and samples were thawed in a water bath at room temperature.

Determination of Freeze-thaw Damage:

After completion of the freeze-thaw cycle samples were centrifugated. After centrifugation (Eppendorfcentrifuge for 3 min at 3000×g) the supernatants were processed for hemolysis measurements. For determination of hemolysis the Cyanmethemoglobin method was applied. Absorption was read at 540 nm using a Hewlett Packard spectrophotometer. Percentage hemolysis was determined by Equation 1, supra. Percentage hemolysis was taken as a measure for freeze-thaw damage. Results are shown in FIG. 2.

Figure 2:
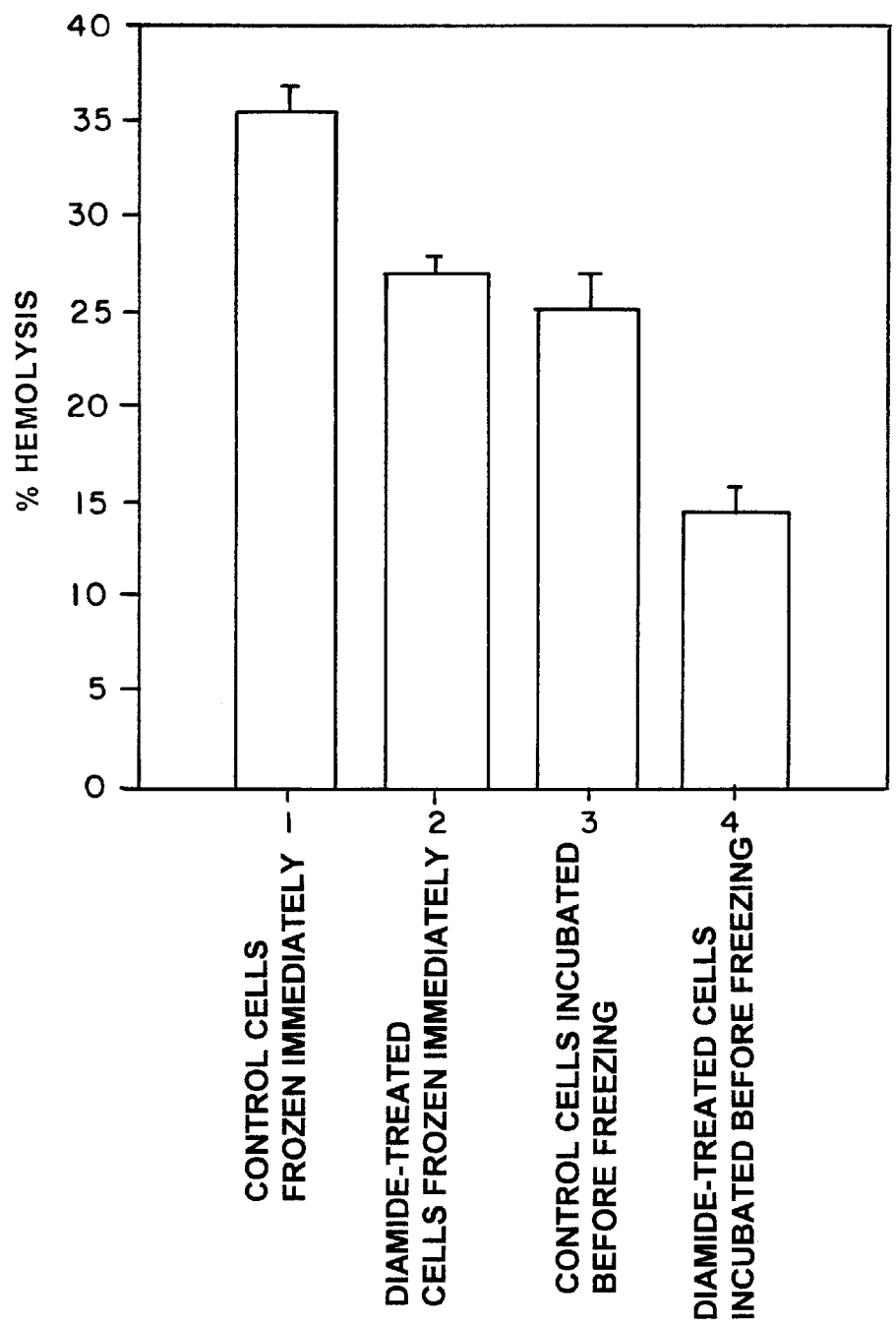
FIG. 2 depicts the percentage hemolysis observed in various samples, under varying conditions, with error bars.

FIG. 2 shows the cryoprotection of erythrocytes by treatment with diamide. Human erytirocytes were pre-treated at room temperature with 5 mM diamide for 1 h. After the incubation was completed the unreacted reagent was removed by a washing procedure and the cells were re-suspended in a freezing medium. Erythrocytes were frozen immediately or after three hours of incubation in the freezing medium to allow loading with glucose. Percentage hemolysis represents the freeze-thaw damage after 1 h freezing at −20° C. in a freezer. Column 1 shows control cells frozen immediately; column 2 shows diamide treated cells frozen immediately; column 3 shows control cells incubated in the freezing medium before freezing; column 4 shows diamide treated cells incubated in the freezing medium before freezing.

Measurement of Deformability:

The deformability of erythrocytes after crosslinking with diamide and its reversal with dithioerythritol is measured using a "gravity-driven" filtration assay. Diluted erythrocyte suspensions are passed through a 5 µm pore filter The relative filtration index is determined using the following expression:

$$RFI = \frac{\text{Volume of erythrocyte suspension filtered at 30 sec}}{\text{Volume of erythrocyte-free suspending medium filtered at 30 sec}}$$

Table 1 shows the effect of crosslinking and its reversal on membrane deformability. Human erythrocytes subjected to crosslinking with diamide and subsequent reversal of the crosslinking dithioeiythritol were passed through a 5 µm pore filter. Relative filtration index was determined.

TABLE 1

| Erythrocyte treatment | Relative filtration index |
| --- | --- |
| Normal erythrocytes | 0.90 ± 0.02 |
| Crosslinking with 5 mM diamide | 0.71 ± 0.03 |
| Reversal of the cross-linking with 5 mM dithioerythritol | 0.83 ± 0.02 |
| Reversal of the cross-linking with 10 mM dithioerythritol | 0.90 ± 0.01 |

EXAMPLE 2

TREATMENT OF ERYTHROCYTES WITH DTBP

Materials and Methods

Reazents

Dimethyl-3,3'-dithiobispropionimidate (DTBP) was purchased from Pierce (Rockford, Ill.). Dithioerythritol (DTF), lysolecithin (LPC), trichloroacetic acid (TCA). 3-phosphoglyceric acid (PGA) and NADH were reagent grade or better and obtained from Sigma (St. Louis, Mo.).

Erythrocyte Preparation, Cross-linking Procedure and Cross-linking-reversal Procedure Packed human erythrocytes from healthy donors were obtained from the National Naval Medical Center (Bethesda, Md.) within 48 h of donation and used within 7 days. Packed erythrocytes were washed twice in phosphate buffer solution (PBS) then re-suspended in PBS (1 vol PBS:1 vol packed cells). The erythrocyte suspension (100 ml) was placed on ice and carbon monoxide (CO) was bubbled through it for 2 hours. Saturation with CO (100%) was achieved under these conditions as detected with a CO-oximeter. Erythrocytes were packed and cross-linked with DTBP at 4° C. for different incubation times (from 1 to 24 h; 9 vol cross-linking solution: 1 vol packed cells). The cross-linking solution was prepared by dissolving DTBP in PBS (pH 7.8). After incubation DTBP was removed by repeated washing of the red cells in PBS (IEC Centra centrifuge for 10 min at 1008×g). Reversal of the cross-linking was carried out at room temperature with the reducing agent dithioerythritol (DTT) at a concentration of 10 mM in PBS (9 vol reducing solution: 1 vol packed cells) for 20 min or as indicated in the figure legends. DTT was removed by repeated washing of the red cells in PBS (IEC Centra centrifuge for 10 min at 1008×g). CO-treatment was reversed at room temperature using a hollow fiber membrane oxygenator model Capiox 308. Erythrocytes were processed through the oxygenator for 1 h. Saturation with oxygen (92%) was reached as detected with a CO-oximeter.

Testing

Erythrocyte Stability in Distilled Water

Erythrocytes were cross-linked with DTBP at different concentrations for different incubation times. 1 ml of the erythrocyte suspension was taken out at regular incubation times centrifuged and DTBP was removed (Eppendorf centrifuge for 3 min at 3000×g). Distilled water (1 ml) was added to the remaining packed cells. After 30 min the cells were again centrifugated (Eppendorf centrifuge for 3 min at 3000×g), and the supernatants were processed for hemolysis measurements. For determination of hemolysis the cyanmethemoglobin method was applied (see Brown in "Hematology: principles and procedures" pp. 29–31 (Lea and Febiger, eds., 1984)). Absorbance was measured at 540 nm and percent hemolysis was determined by Equation (1), supra, where the control sample was lysed in distilled water.

Erythrocyte stability in distilled water was tested after crosslinking reversal as well. Red blood cells were first cross-linked with DTBP then treated with DTT at different concentrations (from 1 to 10 mM) for different incubation times (from 5 to 20 min). Hemolysis in distilled water was measured as described above.

Osmotic Fragility Test

An osmotic fragility test (a common clinical test) was performed on erythrocytes cross-linked with 5 mM DTBP for different incubation times and on erythrocytes cross-linked and reversed with DTT. Briefly, 1 ml of the erythrocyte suspension was taken out at regular incubation times, centrifuged, and DTBP or DTT was removed (Eppendorf centrifuge for 3 min at 3000×g). 1 ml of solutions containing buffered sodium sodium chloride at different concentrations (from 1% to 0.1% NaCl in phosphate buffer) were added to the packed cells. After 30 min the samples were centrifugated (Eppendorf centrifuge for 3 min at 3000×g), and the supernatants were processed for hemolysis measurements.

Deformability Measurements

Red blood cells were cross-linked with 5 mM DTBP for 1 h. Cross-linking was reversed with 10 mM DTT for 20 min. Deformability measurements were made with fresh untreated, cross-linked, and reversed cells as well as with untreated packed cells stored in CPDA-1 for 6 weeks at 4° C. The effects of cross-linking and reversal on red blood cell deformability were measured with an ektacytometer (Technicon).

The ektacytometer is a laser diffraction viscometer described in detail by Bessiss and Mohandas. Intact red blood cells and ghosts suspended in solution produce a diffuse circular laser diffraction pattern. The instrument takes advantage of the fact that when a shear force is applied to the solution crossing the beam the cells align in the direction of shear and begin deforming into uniformly oriented ellipsoids. The laser diffraction pattern then takes on an ellipsoidal shape oriented 90° from the major elliptical cell axis, with the ratio of the long axis to the short axis length determined by the degree of cell deformation. A signal proportional to mean cellular ellipticity is derived from photometric measurement of this laser diffraction pattern in the two axis directions and is designated the deformability index (DI).

Two types of deformability profiles were generated in the present experiments. In one, DI was recorded as shear stress continuously increased from 0 to 271 dynes/cm$^2$ (Shear-scan). In the other, shear stress was held constant at 162 dynes/cm$^2$ while osmolality was continuously increased from 63 to 391 mosmol/kg (Osmo-scan). Shear-scans were run with 40 µl of concentrated cell suspension (80% hematocrit) mixed with 3.0 ml of 3.1% (w/v) polyvinylpyrrolidone (P, av-MW 360 kD) solution containing 138 mM NaCl, 6.34 mM Na$_2$HPO$_4$, 2 mM NaH$_2$PO$_4$, and 0.04% (w/v) NaN$_3$ with pH=7.35±0.05, osmolality=290 mOsmol/kg (by freezing point depression), and viscosity=20 cp (assumed). Osmo-scans were run by continuous addition of this suspension medium containing 100 µl of cells to a PVP solution with a graded salt concentration. Salt gradients were made by addition of high salt PVP solution with 386 mM NaCl (osmolality=750 mOsmol/kg) to a low salt PVP solution with 2.5 mM NaCl (osmolality=40 mOsmol/kg). Conductance measurements of the cell suspension in the viscometer provided an indirect measure of osmolality, which was calculated from a standard calibration curve.

Data was recorded onto a computer, and curves were fitted and plotted using custom routines in Matlab (The Math Works Inc, Natick, Mass.). Shear scans were fitted with a polynomial of degree 6 from which the maximum DI ($DI_{max}$) was calculated. Osmo-scans were fitted with a running average, and $DI_{max}$ was calculated within the range of 180–240 mOsmol/Kg, along with the osmolality corresponding to 1/2DImax at hypertonic salt concentrations (0'), where DI decreases with increasing intracellular viscosity secondary to cell shrinkage and increased hemoglobin concentration (see Mohandas et al., *J. Clin. Invest.* 66563–73 (1980)). The osmolality corresponding to the minimum DI ($O_{min}$) at hypotonic salt concentrations, where DI falls due to cell swelling, was also calculated. The height of the small DI peak thought to be associated with the sudden availability of excess membrane for deformation as intracellular ions and water are lost in the lower range of hypotonic salt (63–125 mOsmol/Kg) concentrations was also recorded (see Clark et al., *Blood* 61 899–910 (1983)).

Morphological Studies

Microscopy. Cross-linked and reversed cells were prepared as described in the section on erythrocyte preparation, etc., with the addition of 0.5% bovine serum albumin to the solution prior microscopic examination. Cells were examined using an Nikon Optiphot, equipped with PlanApo 20×objective.

Assay of capacity for shape change. To induce echinocytosis (shrinkage of erythrocytes in hypertonic solution, so that the surface becomes spiky), erythrocytes were incubated with 10µg/ml LPC for 2 min at room temperature. Erythrocytes were pretreated with 5 mM DTBP for 1 h and then subjected to 10 µg/ml LPC treatment. Microscopic examination of cell morphology was performed. Erythrocytes were pretreated with 5 mM DTBP for 1 h, reversed with 10 mM DTT for 20 min and then subjected to 10 µg/ml LPC treatment. Microscopic examination followed. Erythrocyte response to LPC of normal, cross-linked and reversed cells was compared.

Oxygen Carrying Ability

A semi-quantitative measure of oxygen carrying ability by DTBP cross-linked and reversed cells was performed. Red cells cross linked with 5 mM DTBP for different incubation times and cells reversed with DTT (see above) were processed through a membrane oxygenator to replace CO with oxygen. Oxygen saturation of the cells was measured using a CO-oximeter. After the oxygenation, cells were subjected to deoxygenation under a stream of nitrogen for 30 min. Percentage oxygen was measured again by the CO-oximeter. Oxygen binding and releasing properties for cross-linked, reversed and normal cells were compared.

Results

Figure 3:
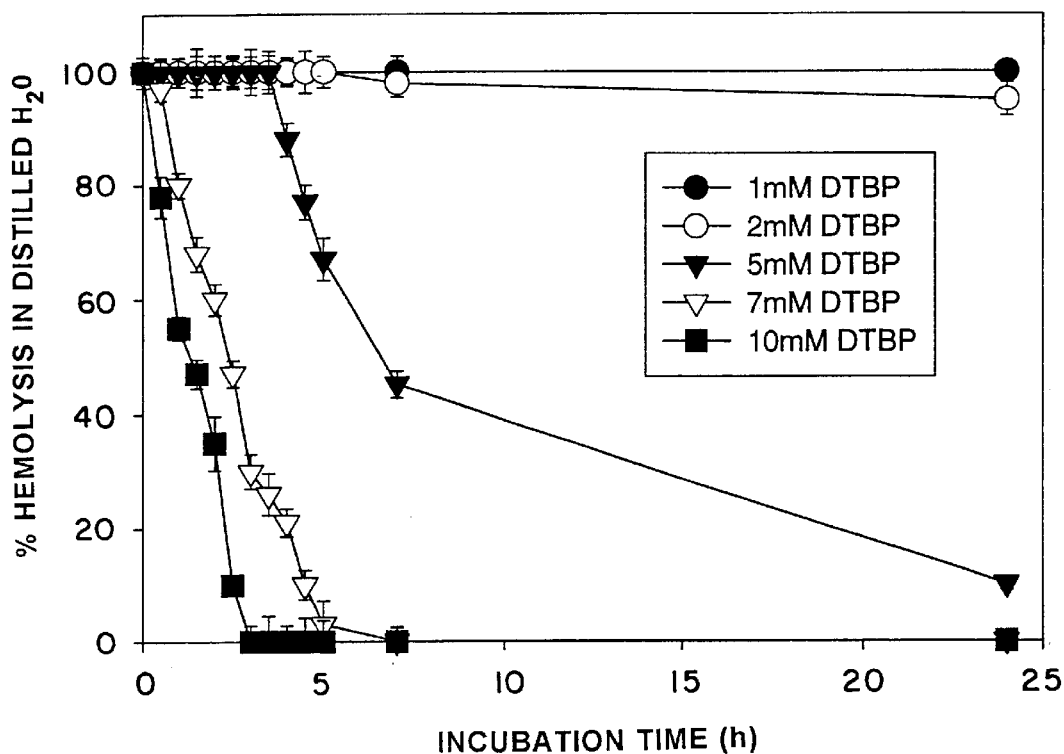
FIG. 3 plots the hemolysis of erythrocytes in $H_2O$ after being incubated with different, concentrations of crosslinking agent for different times.

Effects of Crosslinking and Crosslinking Reversal on Red Blood Cell Stability in Distilled Water Treatment with low concentrations of DTBP such as 1 or 3 mM did not produce cells stable to hemolysis in distilled water even after prolonged incubation times. Increasing DTBP concentration, however resulted in progressive cell stabilization. Treatment with 5, 7 or 10 mM DTBP for 4 h showed a decrease in hemolysis from 88, 21 to 0%. hemolysis in distilled water. At a given DTBP concentration increasing the incubation time resulted in progressive cell stabilization. Cells treated with 5 mM DTBP for 3, 5 or 24 h lysed respectively 100, 67 or 10% in distilled water. Results are summarized in FIG. 3.

Figure 4:
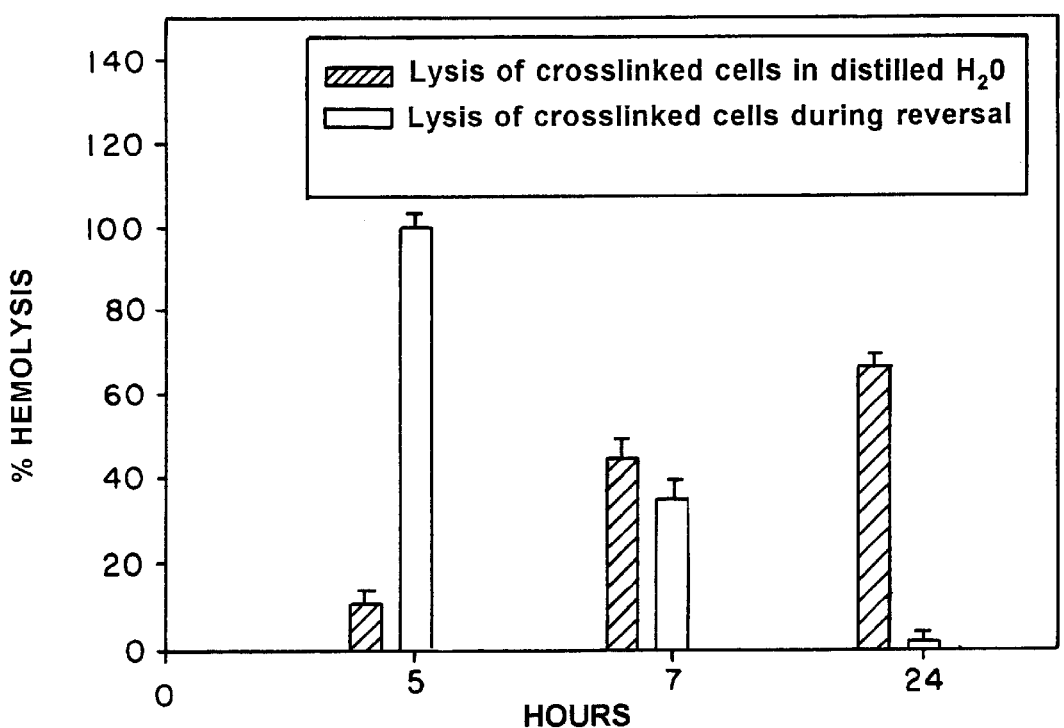
FIG. 4 plots the hemolysis of cross-linked erythrocytes in $H_2O$ before, during, and after reversal of the crosslinking.

Examination of the reversal of cell stabilization in distilled water followed. Red blood cells were cross-linked with 5 mM DTBP for 5, 7 and 24 h to induce a different degree of stabilization. The reducing agent DTT was used to reverse the cross-linking by DTBP. Hemolysis was measured after treatment with DTT was completed and after the reversed cells were resuspended in distilled water. FIG. 4 shows the results of these experiments. Cells with a higher degree of cross-linking or stabilization were extremely unstable in the presence of the reducing agent. Treatment with SmM DTBP for 24 h produced cells that lysed only 10% in distilled water but 100% after the treatment with DTT. Treatment with 5 mM DTBP for 7 h produced cells that lyzed 45% in distilled water and 35% after the treatment with DTT. Cells with a lower degree of stabilization that lyzed 67% in distilled water were stable in the presence of the reducing agent. These cells after the cross-linking reversal lyzed 100% in distilled water. It has to be noted that 100% lysis of the cells in distilled water was achieved after treatment with 10 m DTT for 20 min. Lower concentrations of DTT and shorter incubation times only partially recovered the ability of red cells to lyse in distilled water (data not shown). These results show that cross-linking reversal to recover cell ability to lyse 100% in distilled water is in fact possible. It depends however on the degree of stabilization induced. Our interest was drawn to conditions of cross-linking which produced cells only partially stable in distilled water such as treatment with 5 mM DTBP for 5 h or less.

Figure 5A:
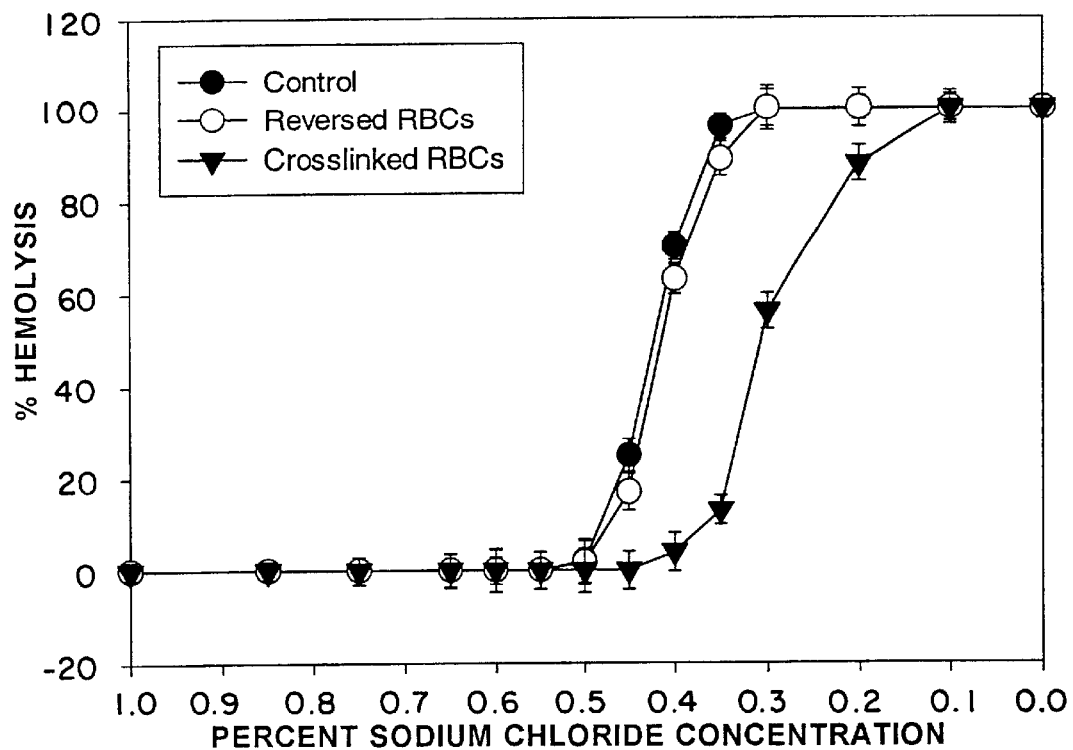
FIGS. 5A and 5B plot the osmotic fragility of erythrocytes.
Figure 5B:
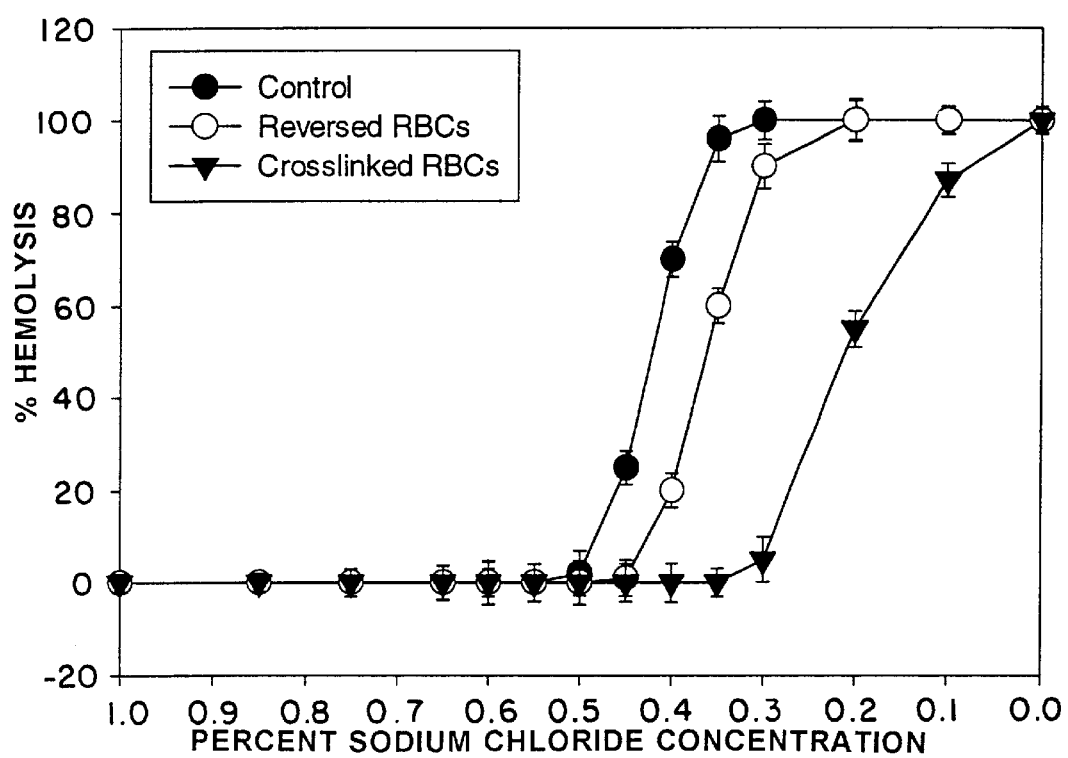

Effects of Cross-linking and Cross-linking Reversal on Red Blood Cell Osmotic Fragility Osmotic fragility results are shown in FIGS. 5A and 5B. Red blood cells were cross-linked with 5 mM DTBP for 1 hr (FIG. 5A) or 3 hr (FIG. 5B) then reversed with DTT. Osmotic fragility was measured for normal, cross-linked, and reversed cells. As seen in FIGS. 5A and 5B, cross-linking significantly reduced red cell osmotic fragility. This effect was more pronounced in cells treated for 3 with DTBP compared to these treated for only 1 h. For controls hemolysis (2–3% hemolysis) was detected at 0.5% NaCl. For 1 or 3 h cross-linked cells hemolysis started at 0.4 or 0.30% NaCl respectively. Control cells lysed 100% at 0.3% NaCl, while for 1 or 3 h cross-linked cells total lysis was first measured at 0.1 or 0.0% NaCl. Reversal of the cross-linking with DTT in both cases resulted in reversal of the effect of DTBP on cell osmotic fragility. However, complete reversal of red cell osmotic fragility was observed only for cells treated for 1 h with DTBP.

Effects of Cross-linking and Cross-linking Reversal on Red Cell Shape

When normal red blood cells were incubated with 10µg/ml LPC they underwent a shape change from discocytes to echinocytes. Cross-linking with 5 mM DTBP for 1 h however completely blocked this effect of the echinocytosis producing agent LPC Red cells pretreated with DTBP remained biconcave discs in the presence of LPC This shape stabilizing action of DTBP was completely reversible after cross-linking reversal with DTT. Cells cross-linked with DTBP and then reversed with DTT underwent shape changes from discocntes to echinocytes when treated with LPC as normal cells do. It should be noted that cross-linking with DTBP and cross-linking reversal with DIT preserved the normal biconcave red cell shape.

Effect of Cross-linking and Cross-linking Reversal on Red Cell Deformability

Figure 6:
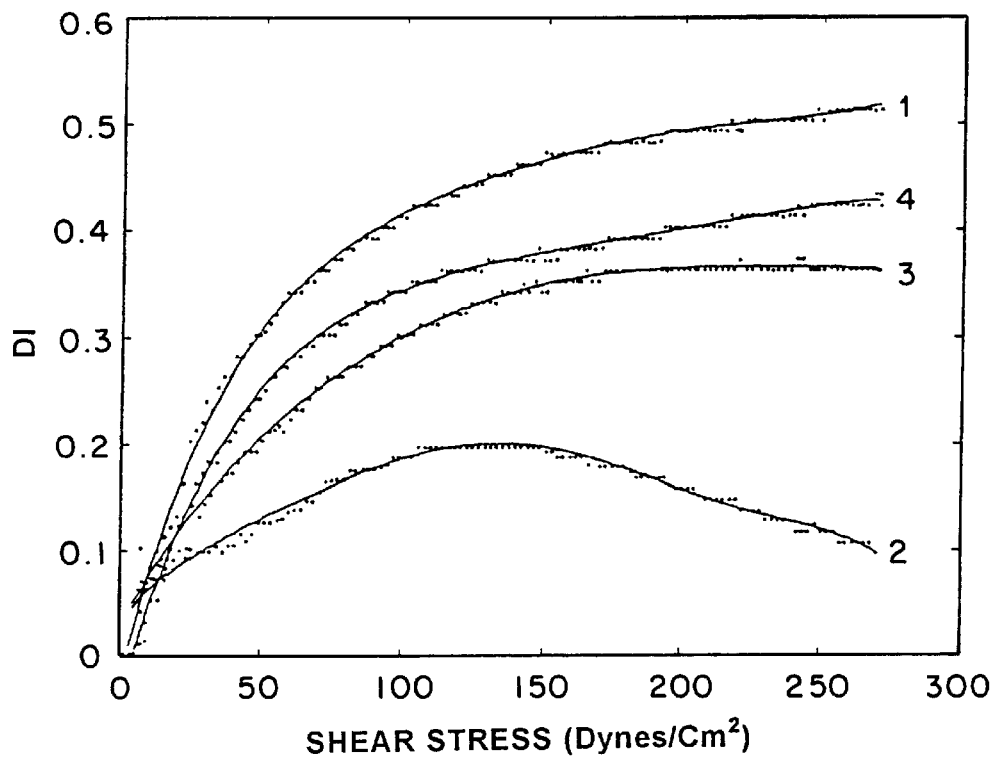
FIG. 6 plots DI versus shear stress.

Treatment with 5 mM DTBP for 1 h reduced red cell deformability as a function of shear stress by over half (FIG. 6) and altered the shape of the response curve. For both FIGS. 6 and 7, the traces are for untreated erythrocytes (1), erythrocytes cross linked with DTBP (2), erythrocytes with their crosslinking reversed by DTT (3), and untreated 6 week old erythrocytes (4). The cross-linked cells appeared to lose stability in the flow field above 150 dynec/cm2, resulting in a continuous decrease in DI as shear stress increased to the end of the run. Reversal of the cross-linking with DTT appeared to stabilize the cells and produced a response to shear stress that, although not normal, was similar to that of 6-week old cells, which are still suitable for transfusion.

Figure 7:
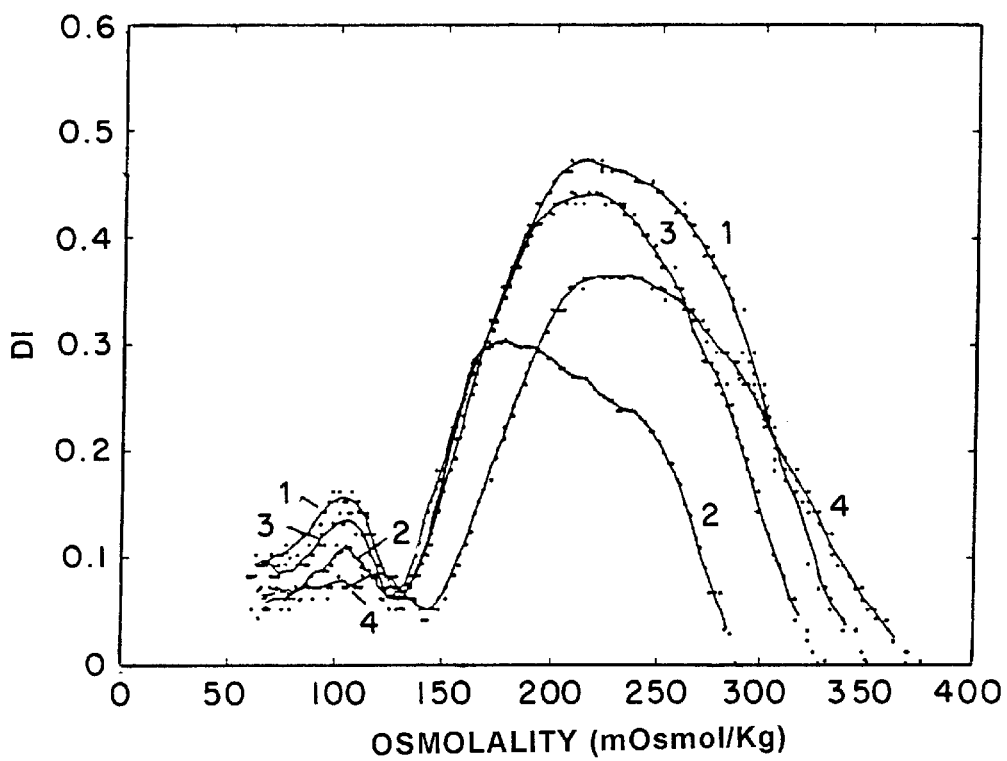
FIG. 7 plots DI versus osmolality.

FIG. 7 presents Osmo-scan data for the same experiment. Treatment with DTBP reduced DImax by 36% (from 0.47 to 0.30) and markedly shifted O' to a lower osmolality (from 302 to 264 mOsmol/Kg). Treatment with DTT restored these indices towards normal values. Cross-linking also caused a slight shift in $O_{min}$ to lower osmolality (125 vs 130 mOsmol/Kg for fresh control cells), which was largely reversed (to 128 mOsmol/Kg) by treatment with DTT. In all three cases the relative heights of the peaks below and above the $O_{min}$ appeared to be well maintained, unlike the 6-wk old cells where the lower peak was almost absent, and $O_{min}$ shifted to a higher osmolality (142 vs 130 mOsmol/Kg for normal cells).

Effect of Cross-linking and Cross-linking Reversal on Red Cell Functionality

The metabolic viability of cross-linked cells was assayed by monitoring the production and depletion of ATP over time. DTBP cells were cross-linked in 5 mM DTBP 150 mM glucose for 5 hours at 4° C. The cells were then washed 3 times and incubated in 150 mM glucose for an additional 19 hrs. After washing to remove the glucose the cells were incubated at 4° C. in PBS for 72 hrs before being returned to 150 mM glucose for the final 24 hr incubation. At each time point cells were removed, washed, and spectrophotometrically assayed for ATP as described in the text. The glucose controls were cells treated in the same manor but without crosslinking, and the control cells are cells without exposure to glucose.

Cross-linked red blood cells remained metabolically active (Table 2). Cells cross-linked for 5 hours with 5 mM DTBP had levels of ATP similar to those of non-cross-linked cells. After 72 hours in PBS at 4° C., the cross-linked and non-cross-linked cells had 51.7 and 51.8 $\mu$mol/dl ATP respectively. While this decrease in internal ATP demonstrates the existence of a similar rate of ATP utilization in the cross-linked and non-cross-linked cells, it does not demonstrate the ability to metabolize glucose for the production of ATP. To confirm the cross-linked red blood cells maintained the ability to produce ATP, glucose was added to the ATP depleted cells. The non-cross-linked glucose control cells showed a return to starting ATP levels of around 70 $\mu$mol/dl after 24 hours. Although the cross-linked cells did not return to starting ATP levels, they did not show the decrease seen in the control cells not exposed to glucose (Table 2). Thus, cells cross-linked with DTBP exhibit metabolic activity, although at a lower level than non-cross-linked cells. The effects of reversal of the DTBP cross-linker was investigated by treating a sample of cross-linked cells with 10 mM DTT prior to the initial exposure to glucose. The DTT exposure did not change the amount of ATP present compared to both the cross-linked and non-cross-linked control cells (data not shown).

TABLE 2

| | ATP Content (? mol/dl) | | |
|---|---|---|---|
| | 24 hrs in glucose | 72 hrs in PBS | 24 hrs in glucose |
| Controls | 72.2 | 27.3 | 19.9 |
| Glucose Controls | 69.8 | 51.8 | 69.9 |
| DTBP Treated | 76.1 | 51.7 | 51.5 |

We measured oxygen content (Vol%$O_2$) of cells subjected to cross-linking and reversal with a CO-oximeter 282. Control samples displayed 8.0 Vol%$O_2$. Cells subjected to CO-treatment showed 0.7 Vol%$O_2$. CO-treated and cross-linked cells with 5 mM DTBP for 5 h, which underwent re-oxygenation in the membrane oxygenator had oxygen content of 7.3 Vol%$O_2$. Re-oxygenated red blood cells were then deoxygenated with nitrogen and displayed a oxygen content of 2.9 Vol%$O_2$. Oxygen content of the reversed cells was similar to that of the cross-linked cells. These results show that cross-linked and reversed cells were able to undergo reversible oxygenation.

Obviously, many modifications and variations of the present invention are possible in light of the above teachings. It is therefore to be understood that, within the scope of the appended claims, the invention may be practiced otherwise than as specifically described.

What is claimed is:

1. A shape stabilized erythrocyte obtained by a method consisting of:

treating erythrocyte with CO gas;

reacting said erythrocyte with a reversible cross-linking agent in the presence of a high concentration of a low molecular-weight cryoprotectant; and lyophilized said erythrocyte;

wherein said reversible cross-linking agent is selected from the group consisting of diamide and dimethyl-3, 3'-dithiobispropionimidate (DTBP), wherein said crosslinking-agent is reacted at a concentration of from about 5 mM to about 10 mM from about 1 hour to about 5 hours, wherein said erythrocyte is suspended in a loading medium, incubated and resuspended in a lyophilization medium prior to said lyophilization, wherein said low molecular weight cryoprotectant is selected from the group consisting of glucose, fructose, sucrose, trehalose, raffinose and combinations thereof, and wherein said high concentration of said low molecular weight cryoprotectant is of from about 500 mM to about 800 mM.

2. The erythrocyte of claim 1, wherein said crosslinking results in disulfide moieties.

3. A population of erythrocytes comprising more than one of said erythrocyte of claim 1.

4. The population of claim 3, wherein at least 80% of said erythorcytes maintainviability after storage.

5. The population of claim 3, wherein at least 90% of said erythorcytes maintain viability after storage.

* * * * *